(12) United States Patent
Tucker

(10) Patent No.: US 11,185,606 B1
(45) Date of Patent: Nov. 30, 2021

(54) ODOR TREATMENT DISPENSER

(71) Applicant: Jeffrey E. Tucker, Sarasota, FL (US)

(72) Inventor: Jeffrey E. Tucker, Sarasota, FL (US)

(73) Assignee: Jeffrey E. Tucker, Sarasota, FL (US)

( * ) Notice: Subject to any disclaimer, the term of this patent is extended or adjusted under 35 U.S.C. 154(b) by 0 days.

(21) Appl. No.: 16/823,920

(22) Filed: Mar. 19, 2020

Related U.S. Application Data

(62) Division of application No. 15/062,192, filed on Mar. 6, 2016, now Pat. No. 10,646,610.

(60) Provisional application No. 62/129,150, filed on Mar. 6, 2015.

(51) Int. Cl.
  *A61L 9/14* (2006.01)
  *A01K 1/01* (2006.01)

(52) U.S. Cl.
  CPC .............. *A61L 9/14* (2013.01); *A01K 1/0107* (2013.01)

(58) Field of Classification Search
  CPC .............................. A01K 1/0107; A01K 1/035
  See application file for complete search history.

(56) References Cited

U.S. PATENT DOCUMENTS

| | | | |
|---|---|---|---|
| 3,428,026 A | 2/1969 | Sohmers et al. | |
| 3,677,441 A | 7/1972 | Nixon, Jr. et al. | |
| 3,726,437 A | 4/1973 | Siegel | |
| 3,734,057 A | 5/1973 | Lee et al. | |
| 3,793,989 A | 2/1974 | Clark | |
| 4,030,449 A | 6/1977 | Ruddick et al. | |
| 4,729,342 A | 3/1988 | Loctin | |
| 5,184,568 A | 2/1993 | Healey | |
| 5,224,975 A | 7/1993 | Purnell et al. | |
| 5,511,513 A | 4/1996 | Baron et al. | |
| 5,755,181 A | 5/1998 | Petkovski | |
| 6,079,364 A | 6/2000 | Tamba | |
| 6,267,297 B1 | 7/2001 | Contadini et al. | |
| 6,312,507 B1 | 11/2001 | Taylor et al. | |
| 6,997,139 B2 | 2/2006 | Rapp | |
| 7,594,480 B2 | 9/2009 | Cressy | |
| 8,434,426 B2 | 5/2013 | Smith et al. | |
| 8,733,287 B2 | 5/2014 | Huck et al. | |
| 8,887,954 B2 | 11/2014 | Carpenter et al. | |
| 2003/0132254 A1 | 7/2003 | Giangreco | |
| 2003/0192485 A1* | 10/2003 | Opfel | A01K 1/015 119/526 |
| 2004/0231667 A1 | 11/2004 | Horton et al. | |
| 2006/0137619 A1 | 6/2006 | Dodman et al. | |
| 2006/0196438 A1* | 9/2006 | Caputa | A01K 1/0107 119/165 |
| 2006/0225660 A1 | 10/2006 | Cressy | |
| 2010/0047119 A1 | 2/2010 | Cressy | |
| 2014/0366809 A1 | 12/2014 | Huck et al. | |
| 2017/0273273 A1 | 9/2017 | Chou et al. | |

* cited by examiner

*Primary Examiner* — Christopher D Hutchens

(74) *Attorney, Agent, or Firm* — Maier & Maier, PLLC

(57) ABSTRACT

An odor treatment dispenser is disclosed for an odor. The device comprises a housing having a canister channel. An aperture traverses the housing. A canister contains an odor treatment substance positioned within the canister channel. An actuator engages the canister for dispensing the odor treatment substance through the aperture for treating the odor.

12 Claims, 12 Drawing Sheets

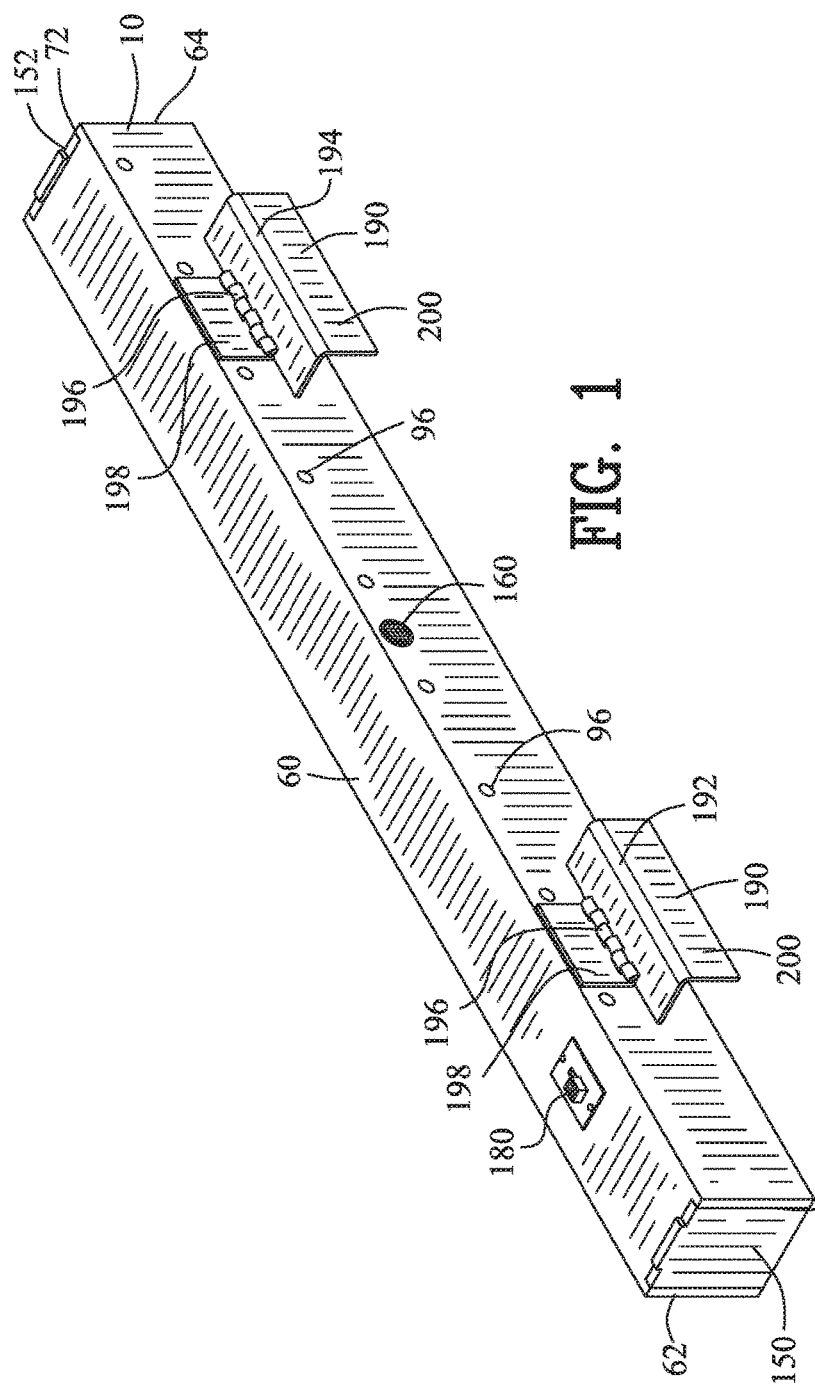

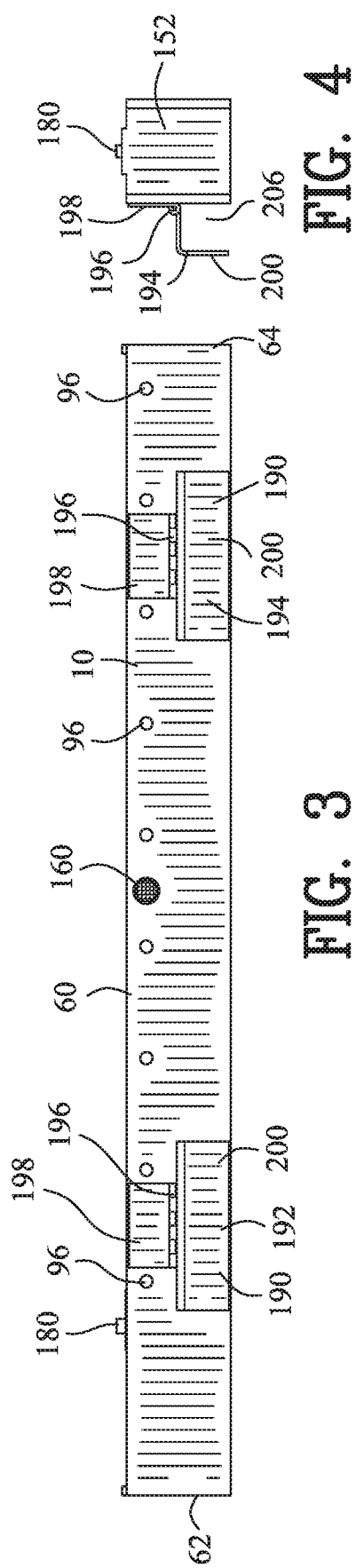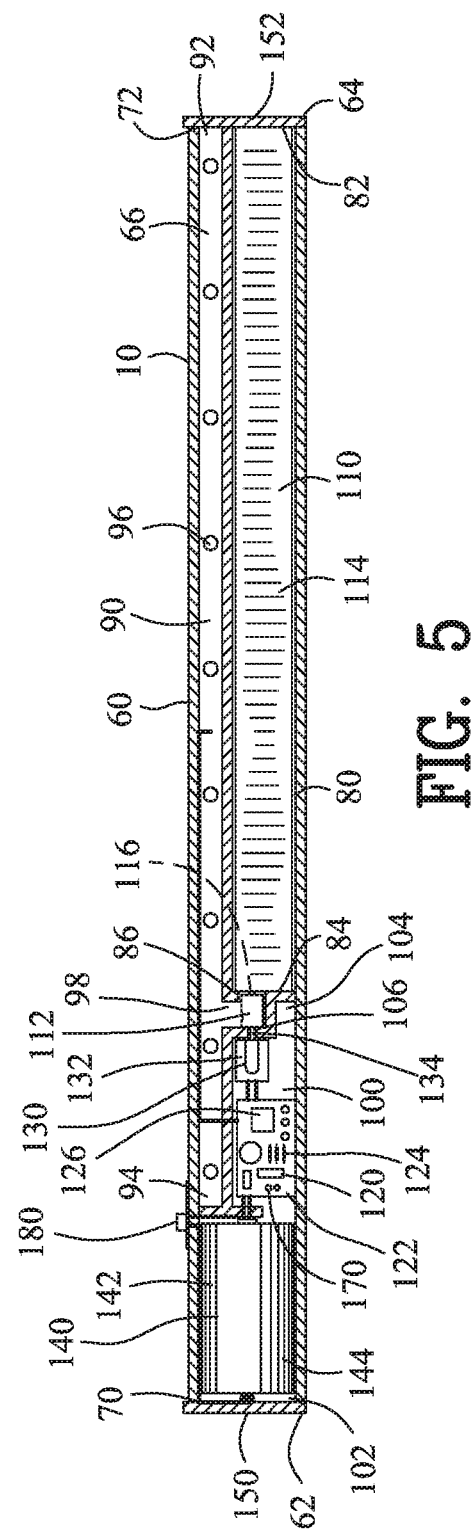

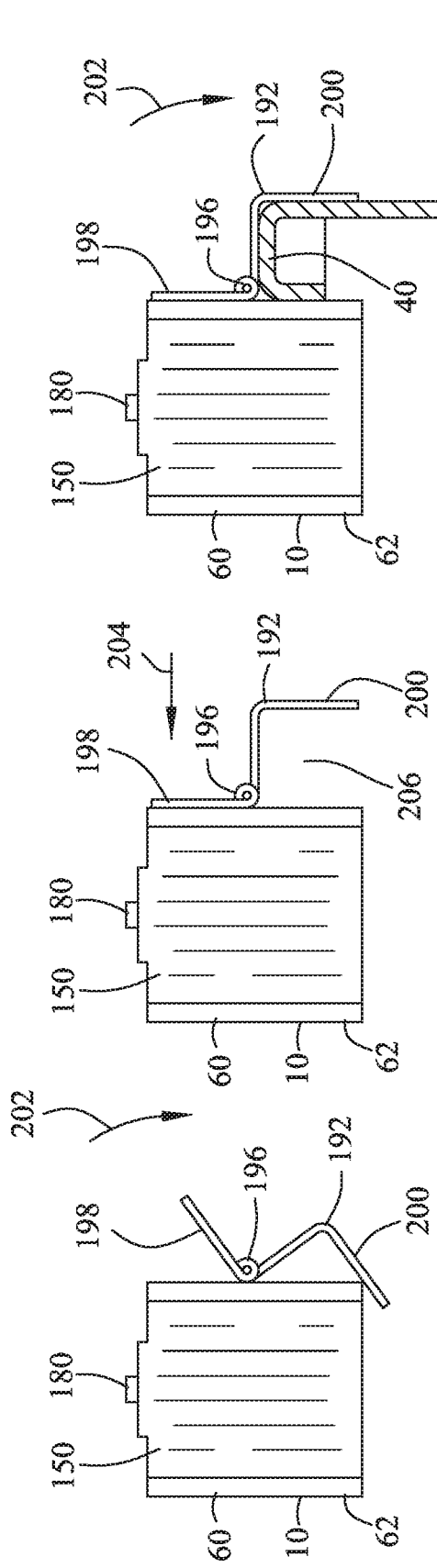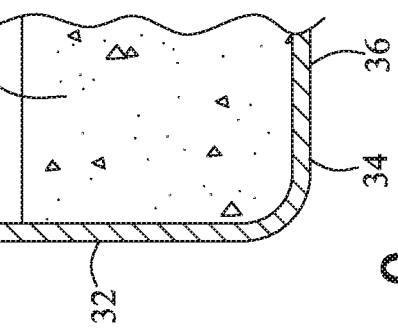

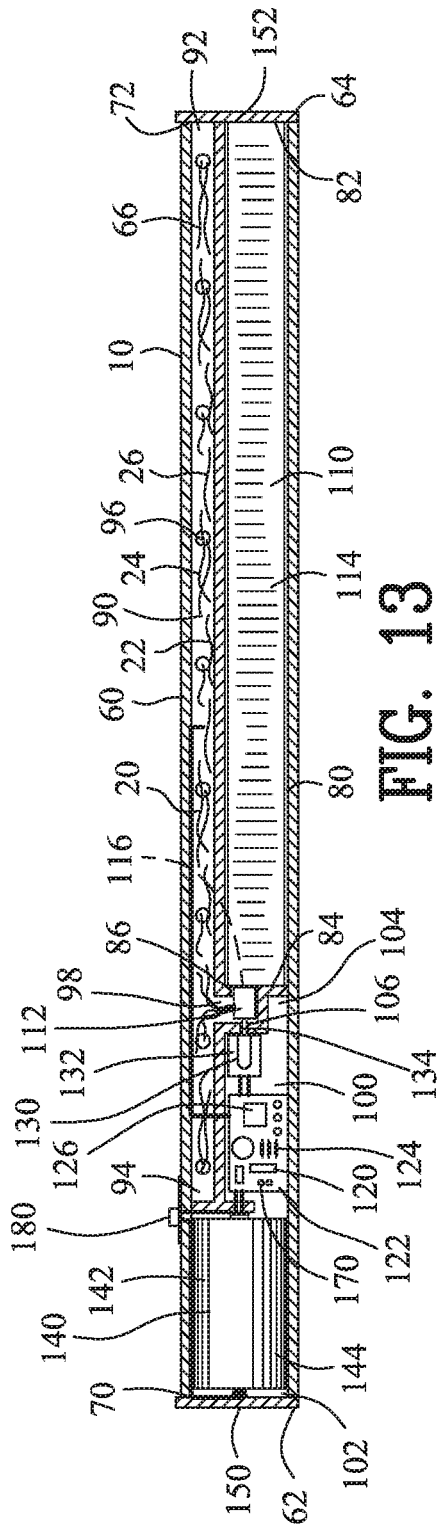
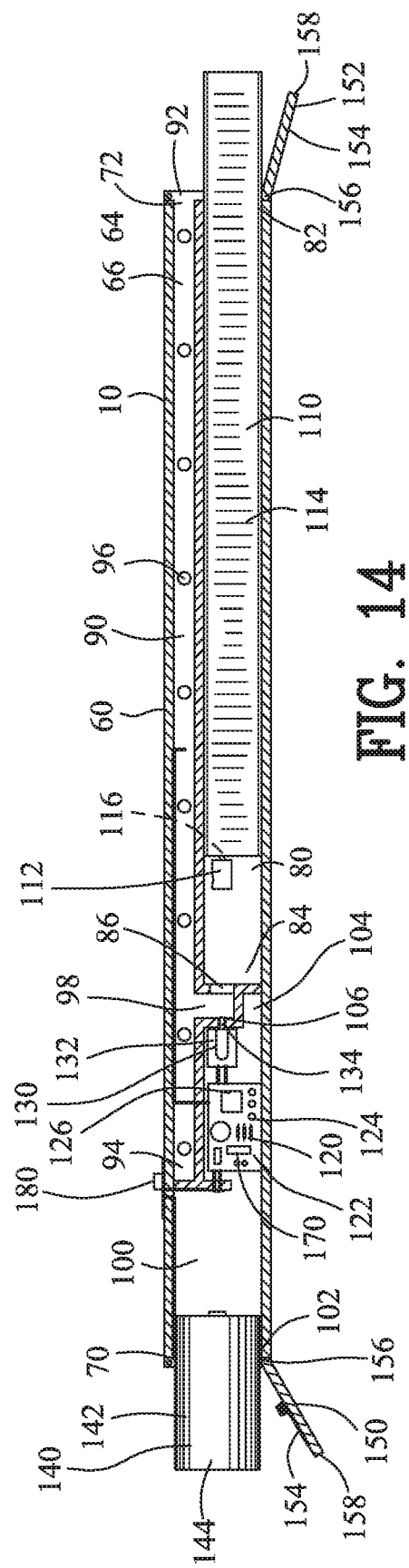
FIG. 13
FIG. 14

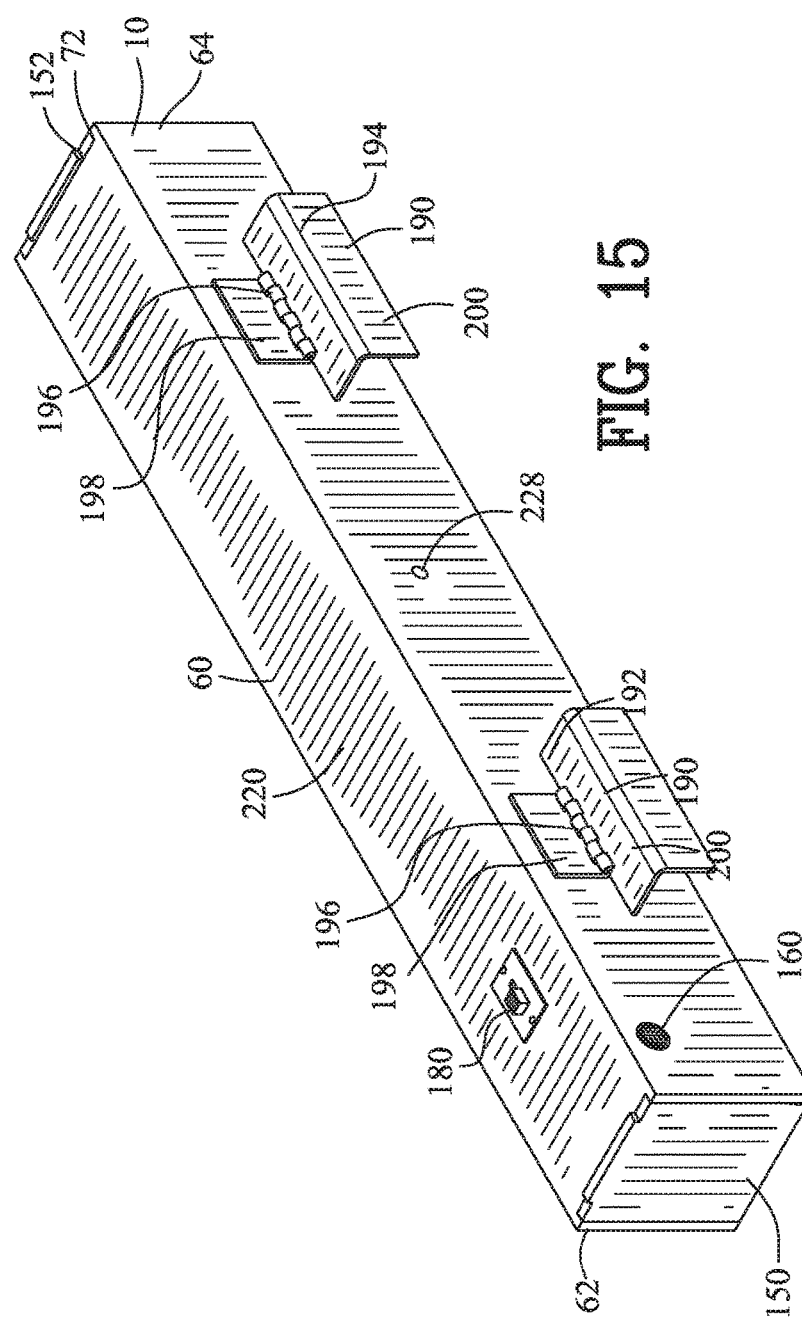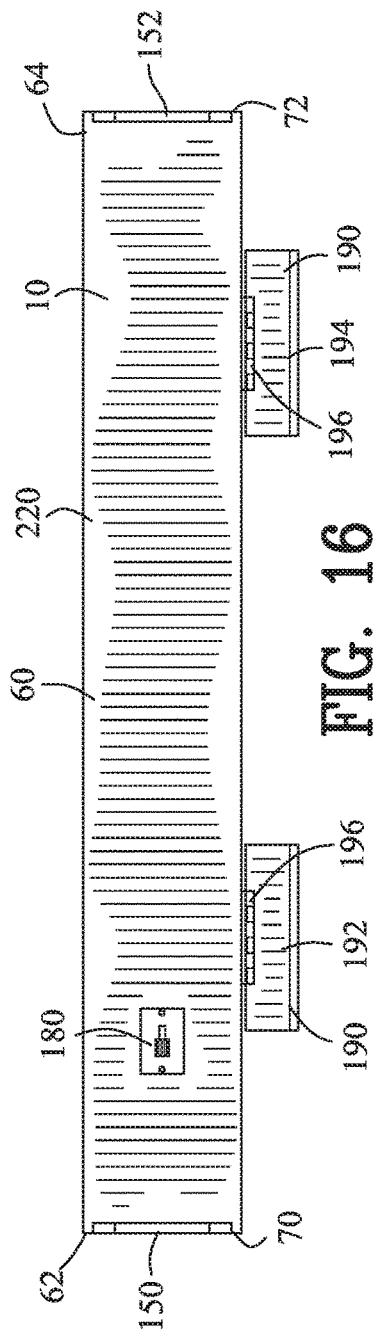

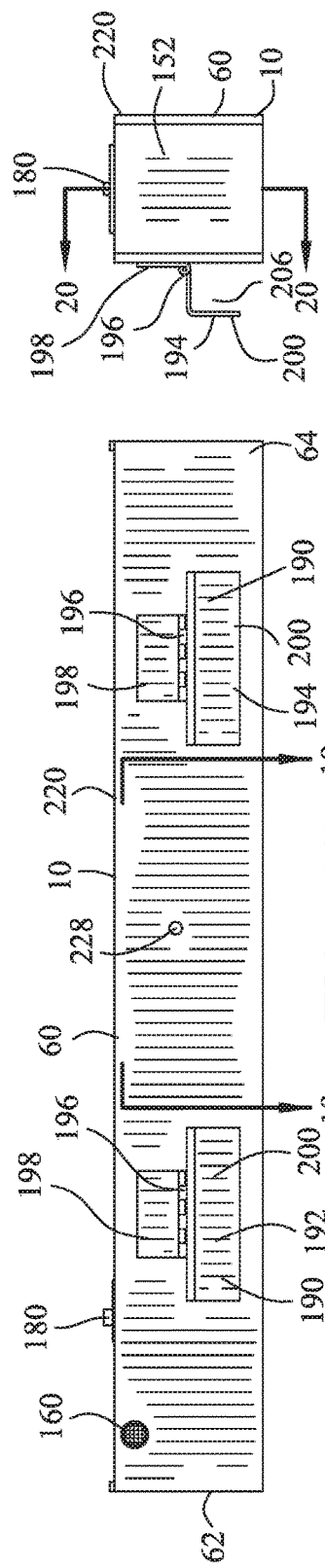
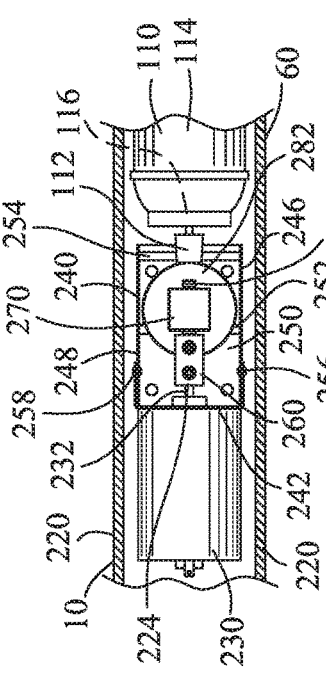
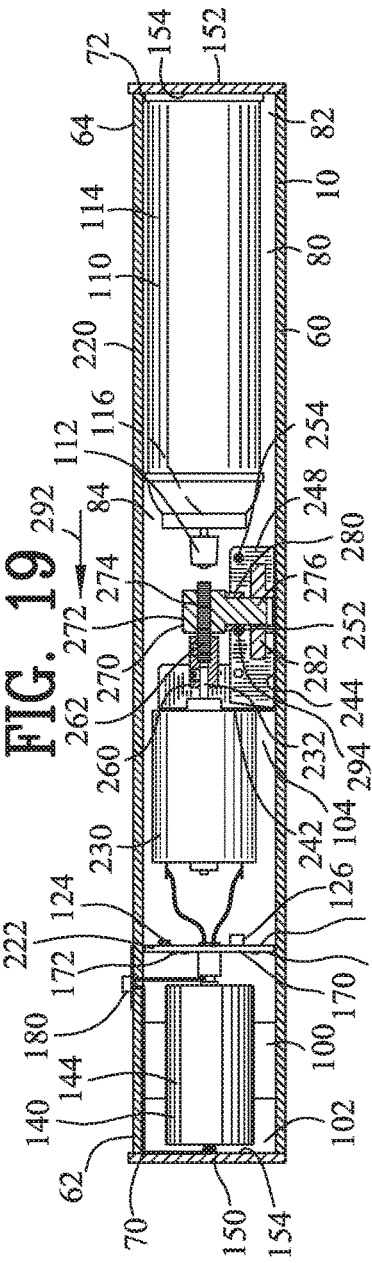

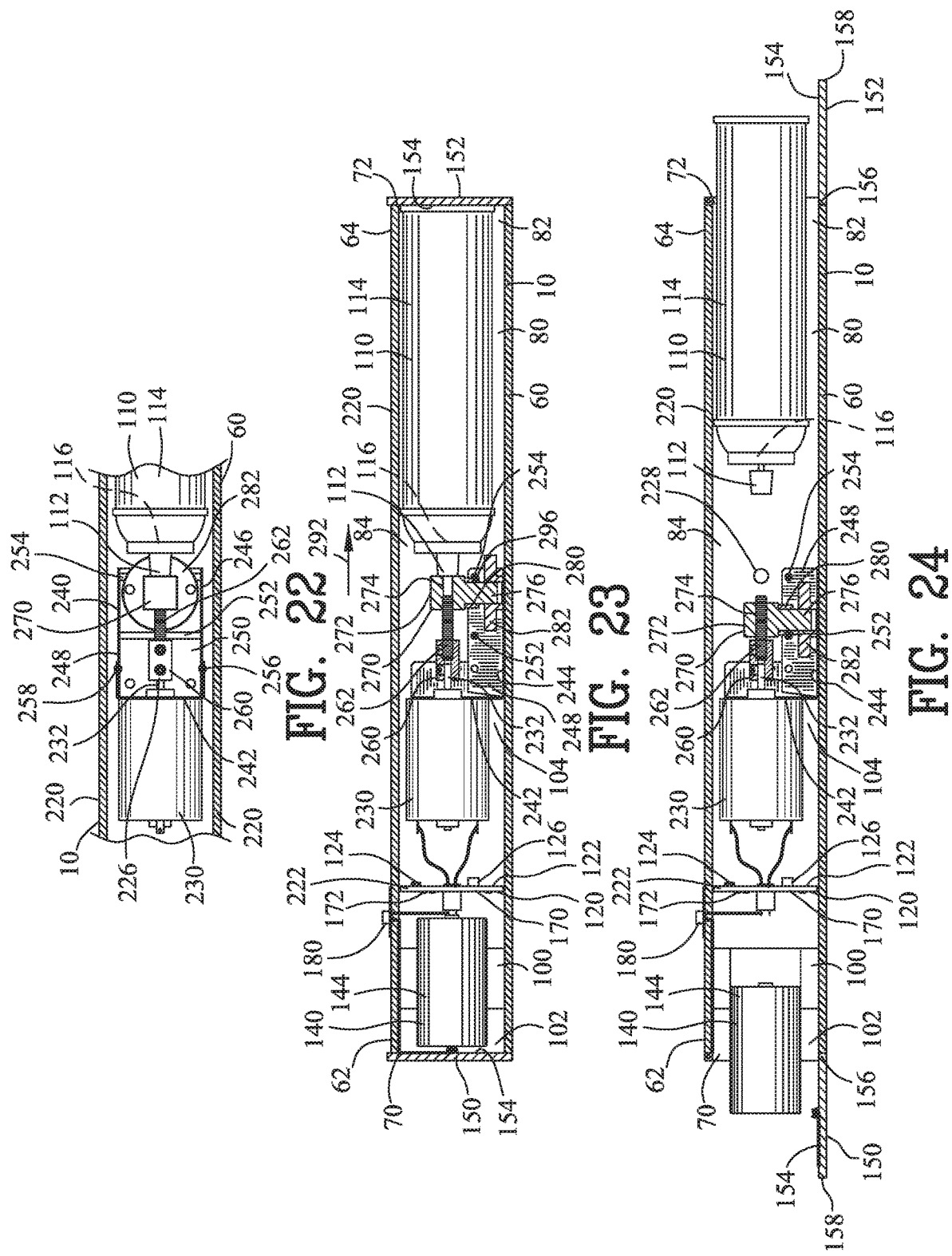

ODOR TREATMENT DISPENSER

CROSS REFERENCE TO RELATED APPLICATIONS

This application claims the benefit of priority under 35 USC 120 as a divisional of U.S. patent application Ser. No. 15/062,192 filed Mar. 6, 2016, entitled ODOR TREATMENT DISPENSER, which claims priority to U.S. Provisional Patent Application No. 62/129,150 filed Mar. 6, 2015, the entire contents of which are hereby incorporated by reference.

BACKGROUND OF THE INVENTION

Field of the Invention

This invention relates to odor control and more particularly to an odor treatment dispenser device.

Background of the Invention

Prior to 1940, cats were generally considered outdoor pets. The few persons allowing cats to remain indoors had to provide sanitary facilities which typically included sawdust, soil, sand and like. These materials did little to hide the odors resulting from use of the "sanitary pan". In 1940, a highly absorbent clay was adapted to use in the "sanitary pan", thus, kitty litter was invented. Although primarily considered to be used by cats, other domesticated pets may also use these types of facilities. Further development led to clumping litter, the addition of a variety of deodorant materials and today many variations of litter exist. Additionally, the development of a wide variety of "cat boxes" to contain the litter have appeared in the marketplace, as is well known to those skilled in the art.

Though these advances have improved the well being of the household cat an/or other domesticated pets, removal of waste from the litter box has remained a problem.

There have been many in the prior art who have attempted to solve these problems with varying degrees of success. None, however completely satisfies the requirements for a complete solution to the aforestated problem. The following U. S. Patents are attempts of the prior art to solve this problem.

U.S. Pat. No. 3,428,026 to Sohmers, et al. discloses a fumigated pet house having a shallow pan-like base, and a superstructure removably mounted on the base. The superstructure includes side walls, a front wall with an entrance opening therein, a rear wall and a roof. The bottom of the superstructure is open to expose the pan-like base to the space within the superstructure. The base is formed of opaque plastic material. The superstructure is formed of transparent plastic material and the roof being gabled and formed with a central straight portion and fumigating means supported on the superstructure to fumigate the interior of the house. The base and superstructure are rectangular in plan, with the base having upstanding side and front and rear end walls and being open at the top. The superstructure includes posts extending upwardly from the corners of the base, rails along the inner surfaces of the side walls and front and rear end walls of the base, adjacent the top edges thereof. The side walls of the superstructure rest on the rails on the side walls of the base, and the end walls of the superstructure rest on the rails on the end walls of the base. The side and end walls of the superstructure are secured at their side edges to the corner posts. The adjacent ends of the side and end walls on the base are spaced from each other, and the bottom of the corner posts extend below the side and end walls of the superstructure into the space between the side and end rails in interlocking engagement with the ends of the side and end rails.

U.S. Pat. No. 3,677,441 to Nixon, Jr., et al. discloses aerosol bombs of the type having a cylindrical body portion and a neck dispensing portion with a collar and a dispensing valve. A mounting bracket and plural dispensers for mounting two or more aerosol bombs are provided with a motor activated dispensing mechanism which depresses the bomb valves, so as to discharge the bombs simultaneously or sequentially at pre-selected time intervals.

U.S. Pat. No. 3,734,057 to Lee, et al. discloses a pet toilet for receiving and then automatically flushing therefrom matter excreted by a pet. The toilet includes an enclosure having walls extending upwardly from a floor and having access means, such as an opening in a sidewall thereof, for a pet to enter and exit from the enclosure. A drainage outlet is provided in the floor and at least a portion of the upper surface of the floor is inclined downwardly toward the outlet. A flush system serves to spray water into the enclosure so that matter excreted therein by a pet is washed from the walls and floor of the enclosure so as to exit through the outlet. Water is supplied to the flush system from a suitable water source when a water supply valve is actuated. A photoelectric system serves to detect a pet entering the enclosure through the access thereto, and an electrical control responds to the photoelectric system for actuating the valve. The control circuit and photoelectric system are arranged so that the enclosure is flushed after the pet has exited. A water timer is provided for controlling the time duration that water is sprayed into the enclosure.

U.S. Pat. No. 3,793,989 to Clark discloses a pet house including means for distributing deodorizer throughout the pet house and means for retaining the odors and deodorizer smell within the confines of the pet house. An electric powered fan may circulate and distribute deodorizer. Deodorant may be a solid, a semi-solid, or a liquid deodorizer fed through a wick from a container supplied with liquid deodorant, or deodorizer may be automatically dispensed by a timed aerosol dispenser. The top of the pet house which is removeable serves to retain the odors and deodorizer smell within the pet house and to prevent contamination of the ambient atmosphere. Removal of the top of the pet house affords ready access to the interior of the pet house for purposes of cleaning, changing cat litter absorbent material, changing batteties in the deodorizer unit, and adding deodorant. The deodorizer unit is attached to the inside of the pet house.

U.S. Pat. No. 4,729,342 to Loctin discloses an automatic pet toilet having a housing defining a generally closed chamber with a floor and side walls, one of the latter having an opening through which the pet can pass. A door is displaceable on the housing between a closed position blocking the opening and an open position clear of same by means of a door drive motor. A closed-door switch on the housing generates an output only when the door is in its closed position. Floor and wall sprays respectively directed in the chamber at the floor and walls of the chamber are supplied with wash liquid, usually water, by a valve connectable to a source of pressurized liquid. A drain in the floor and a chopper connectable to a waste line receive material washed by the sprays from the walls and floor, comminute the material, and feed it to the waste line. A sensor emits an output when the pet is within the chamber and a controller connected to the chopper, switch, sensor, motor, and valve closes the door and then opens the valve and operates the chopper when a pet has entered and left the chamber with interruption of the beam while in the chamber, and thereafter closes the valve, stops the chopper, and opens the door.

U.S. Pat. No. 5,224,975 to Purnell, et al. discloses a deodorizing device for use in a pet's litter box. The deodorizing device has a container body having an open end, a closed end and a cylindrical side wall defining a cavity therein. Chunks of zeolite are disposed within the cavity and retained within the container body by a sealing mechanism. The cylindrical side wall of the container body have a plurality of substantially uniform-sized apertures disposed thereon to permit exposure of the retained zeolite to the odors. A sealing mechanism may be permanently or releasably attached to the container body. A securing mechanism secures the deodorizing device to a structure within the malodorous environment. The zeolite after use can be recharged by exposing to fresh air, sunlight and heat and then reused. In addition to being used in a pet's litter box, the device can be used in many environments, including animal containment areas, living areas, production areas, food storage areas, work areas and automobiles.

U.S. Pat. No. 5,511,513 to Baron, et al. discloses a pet waste material collector and odor eliminator system having in combination a rectangular container, a removable tray insertable in the container which holds litter material and has vents disposed around the upper vertical portions thereof, a filter pack, a fragrance dispenser, and a fan. The tray forms an air chamber between the bottom of the container and the bottom and sides of the removable tray. The fan pulls air and odors across the litter bed material, through the vents of the removable tray into the air chamber, through the air chamber and through a filter pack which absorbs the odors. The air is then pulled across an optional fragrance dispenser which masks any residual odors. The litter box also has a motion sensor device which automatically shuts off the fan as the pet approaches the litter box usually about 10 feet from the litter box.

U.S. Pat. No. 5,755,181 to Petkovski discloses an electromechanical animal waste container for deodorizing fumes from animal waste. The container includes an open frame, a tray, a fume hood and a sensor. The frame has a base and the tray is positioned therein. The tray is for receiving animal waste. The fume hood is attached to the frame and is spaced above the tray. The fume hood has an outlet port formed therein. A fan is positioned in the fume hood such that the fan draws the fumes from the tray into the fume hood and toward the outlet port. The sensor determines when there is an animal in the tray. A control circuit is operably connected to the sensor and the fan wherein when the sensor detects an animal in the tray the fan is switched on after a preselected amount of time and then after a second preselected amount of time the fan is switched off. Preferably a filter is positioned over the outlet port and is for deodorizing air that passes therethrough. Preferably a second filter is positioned at the bottom of fume hood.

U.S. Pat. No. 6,079,364 to Tamba discloses a cat litter-tray for collection and disposal of cat excreta having a tray in which a layer of granules is disposed. A sensor, connected through a delay-timer to a programmer, senses the presence of a cat. The tray includes a door mechanism having a mechanism for hermetic sealing and re-opening of the tray, a water inlet for providing water onto the granules, an air heater for heating granule drying air, a detergent reservoir, a water heating element, and an electric pump for circulating water into the granules through a plurality of nozzles supported on the base of the tray.

U.S. Pat. No. 6,312,507 to Taylor, et al. discloses a hand-holdable electro-kinetic electro-static ionic air freshener-conditioner for a pet shelter or litter box includes a self-contained ion generator that provides electro-kinetically moved air with ions and safe amounts of ozone. The ion generator includes a high voltage pulse generator whose output pulses are coupled between first and second electrode arrays. Preferably the first array comprises one or more pin-like electrodes and the second array comprises one more washer-like electrodes. Preferably a ratio between effective area of an electrode in the second array compared to effective area of an electrode in the first array exceeds about 15:1 and preferably is about 20:1. An electric field produced by the high voltage pulses between the arrays produces an electrostatic flow of ionized air containing safe amounts of ozone. Optionally, a sensor detects odor adjacent the freshener-conditioner causes the ion generator to be activated when sensed odor exceeds a predetermined threshold. Odor-activation of the ion generator can be open or closed loop. A bias electrode, electrically coupled to the second array electrodes, affects net polarity of ions generated. The outflow of ionized air and ozone is thus conditioned.

U.S. Pat. No. 6,997,139 to Rapp discloses An atomization system for odor control in a livestock storage facility includes a reservoir capable of holding a sufficient quantity of an odor control product; a pump in communication with the reservoir; a circulation loop running throughout the livestock storage facility and communicating with the pump and the reservoir; and a plurality of atomization nozzles connected with the circulation loop for distribution of the odor control product onto surfaces of the storage facility and the livestock. The odor control product contains a mixture of vegetable oil, a natural acidic compound, alcohol, and water. Advantageously, the acidic compound in the odor control product is vinegar or concentrated citrus juice. A water supply line is also connected to the circulation loop through a water pump to provide a cooling mist throughout the facility.

U.S. Pat. No. 7,594,480 to Cressy discloses a system for lining a container or the like containing an absorbent, utilizing the liner to contain and direct a treatment fluid into the absorbent to disinfect and renew. A complimentary system to the present invention teaches a deodorization, disinfectant, treatment bin for treating litter infused with animal waste, which treatment bin includes a treatment area utilizing ozone to contain and treat the contaminated litter, rendering same re-useable. The system of the present invention further contemplates an ozone generator having a timer circuit for providing a flow of ozone to the apparatus of the present invention, the ozone generator further contemplating as exemplary features a timer apparatus for providing optimal treatment, as well as a proximity sensor system for sensing the presence of an animal in the litter area, for controlling the ozone generator.

U.S. Pat. No. 8,434,426 to Smith, et al. discloses a pet toilet providing a system where waste is "flushed" into a removable waste reservoir to eliminate waste and pet odors. The pet toilet can include a concave basin, a grating system, a removable water reservoir, and one or more flush tubes. The concave basin can be removably coupled to supporting legs, and can include a drainage hole. The grating system can include one or more grating sections disposed on the concave basin. The removable waste reservoir can be positioned beneath the concave basin and can include an opening aligned with the drainage hole of the concave basin. The removable water reservoir can be connected to one or more flush tubes via a valve. At least one of the one or more flush tubes can be coupled to the concave basin to expel water directly into the concave basin.

Although the aforementioned prior art have contributed to the development of the art of sanitary maintenance of litter boxes, none of these prior art patents have solved the needs of this art.

Therefore, it is an object of the present invention to provide an improved device for the reduction of odors emitted from a litter box.

Another object of this invention to provide an improved device for the reduction of odors emitted from a litter box which automatically operates upon usage by an animal.

Another object of this invention is to provide an improved device for the reduction of odors emitted from a litter box which is easily adapted to existing litter boxes.

Another object of this invention is to provide an improved device for the reduction of odors emitted from a litter box which is easy for the operator to use.

Another object of this invention is to provide an improved device for the reduction of odors emitted from a litter box that is easy to cost effectively produce.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

A specific embodiment of the present invention is shown in the attached drawings. For the purpose of summarizing the invention, the invention relates to an odor treatment dispenser device. An animal producing an odor within the animal container. The odor treatment dispenser device comprises a housing extending between a primary end and a secondary end and defining a housing chamber. The primary end has a primary aperture. The secondary end has a secondary aperture. A canister channel is within the housing chamber and extends between a proximal end and a distal end. The proximal end of the canister channel is coupled to the secondary aperture. The distal end of the canister channel includes a nozzle aperture. A manifold channel is within the housing chamber and extends between a proximal end and a distal end. A plurality of manifold apertures extend from the manifold channel and traverse the housing. An electronic channel is within the housing chamber and extends between a proximal end and a distal end. The proximal end of the electronic channel is coupled to the primary aperture. The distal end of the electronic channel includes an actuator aperture. A canister containing an odor treatment substance is positioned within the canister channel. A nozzle is coupled to the canister and traverses the nozzle aperture. The nozzle dispenses the odor treatment substance from the canister. An electronic controller is positioned within the electronic channel. An actuator is coupled to the electronic controller and traverses the actuator aperture. The electronic controller activates the actuator for depressing the nozzle and dispensing the odor treatment substance through the plurality of manifold apertures and into the animal container for treating the odor.

In a more specific embodiment of the invention, a motion sensor is coupled to the housing for determining the presence of the animal within the animal container. The motion sensor is electrically coupled to the electronic controller for signaling to the electronic controller of the presence of the animal within the animal container.

In a more specific embodiment of the invention, a timer is electrically coupled to the electronic controller. The timer has a timer activation point. The timer activation point is defined by a time interval after the egress of the animal from the animal container. The timer activation point signals to the electronic controller to initiate activation of the actuator for depressing the nozzle.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 1 is an upper front isometric view of a first embodiment for an odor treatment dispenser device of the present invention;

FIG. 2 is a top view of FIG. 1;

FIG. 3 is a front view of FIG. 1;

FIG. 4 is a right side view of FIG. 3;

FIG. 5 is a sectional view along line 5-5 in FIG. 2;

FIG. 7 is a left side view of FIG. 3 illustrating a spring loaded clip in a non-engaged condition;

FIG. 8 is a view similar to FIG. 7 illustrating a force applied to the spring loaded clip for creating a container channel between the spring loaded clip and the housing of the odor treatment dispenser device;

FIG. 9 is a view similar to FIG. 8 illustrating the container channel engaging the animal container for coupling the odor treatment dispenser device to the animal container;

FIG. 13 is a sectional view along line 13-13 in FIG. 12;

FIG. 14 is a view similar to FIG. 13 illustrating the removal of a replaceable battery and a replaceable pressurized aerosol cartridge from the odor treatment dispenser device;

FIG. 15 is an upper front isometric view of a second embodiment for an odor treatment dispenser device of the present invention;

FIG. 16 is a top view of FIG. 15;

FIG. 17 is a front view of FIG. 15;

FIG. 18 is a right side view of FIG. 17;

FIG. 19 is a sectional view along line 19-19 in FIG. 17;

FIG. 20 is a sectional view along line 20-20 in FIG. 18;

FIG. 22 is a view similar to FIG. 19 illustrating an actuator empresses upon an aerosol actuator for dispensing the odor treatment substance;

FIG. 23 is a view similar to FIG. 20 illustrating the actuator empresses upon the aerosol actuator for dispensing the odor treatment substance; and FIG. 24 is a view similar to FIG. 20 illustrating the removal of the replaceable battery and the replaceable pressurized aerosol cartridge from the odor treatment dispenser device.

Similar reference characters refer to similar parts throughout the several Figures of the drawings.

DETAILED DISCUSSION

Figure 6:
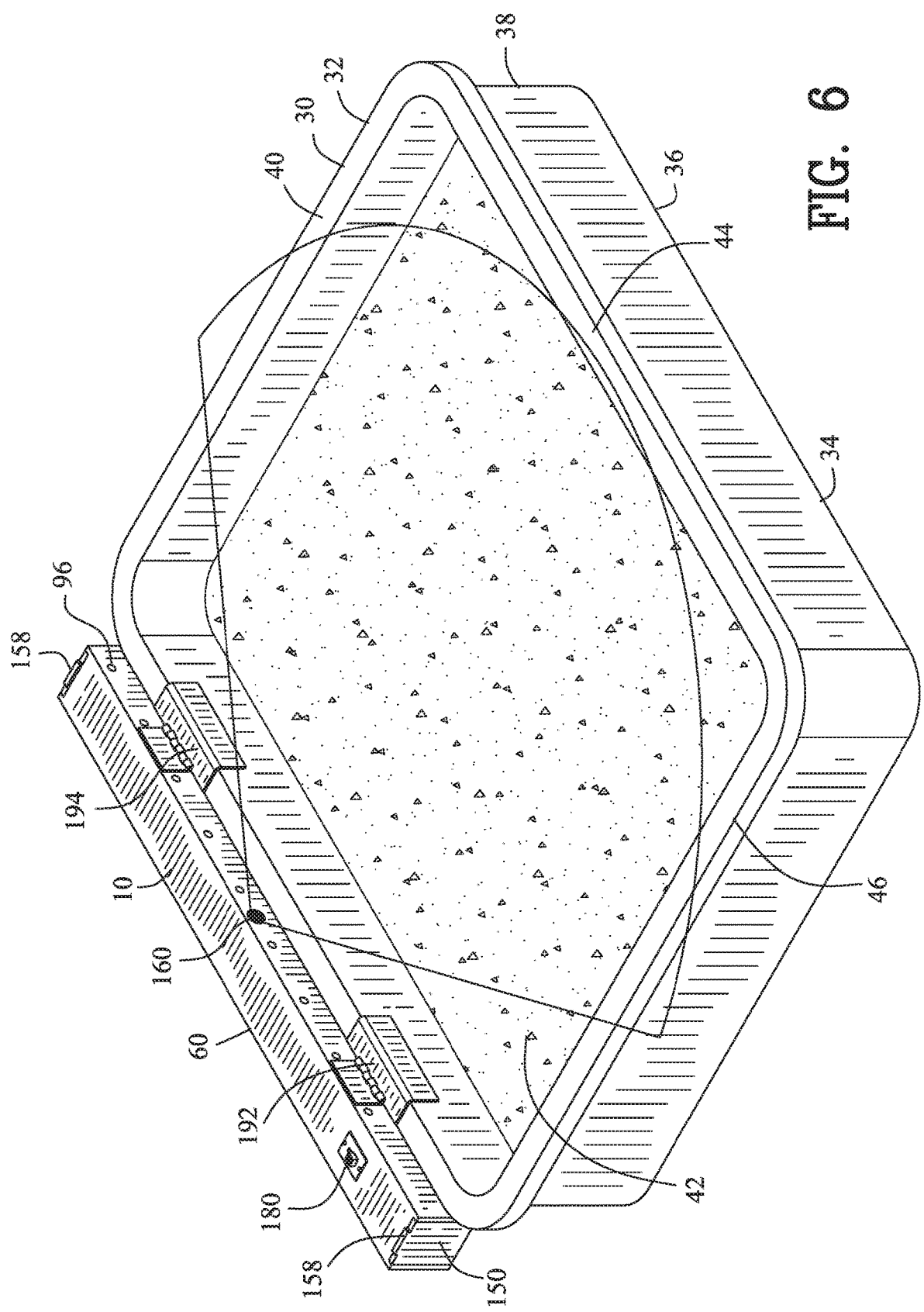
FIG. 6 is a view similar to FIG. 1 with the odor treatment dispenser device engaging an animal container.
Figure 10:
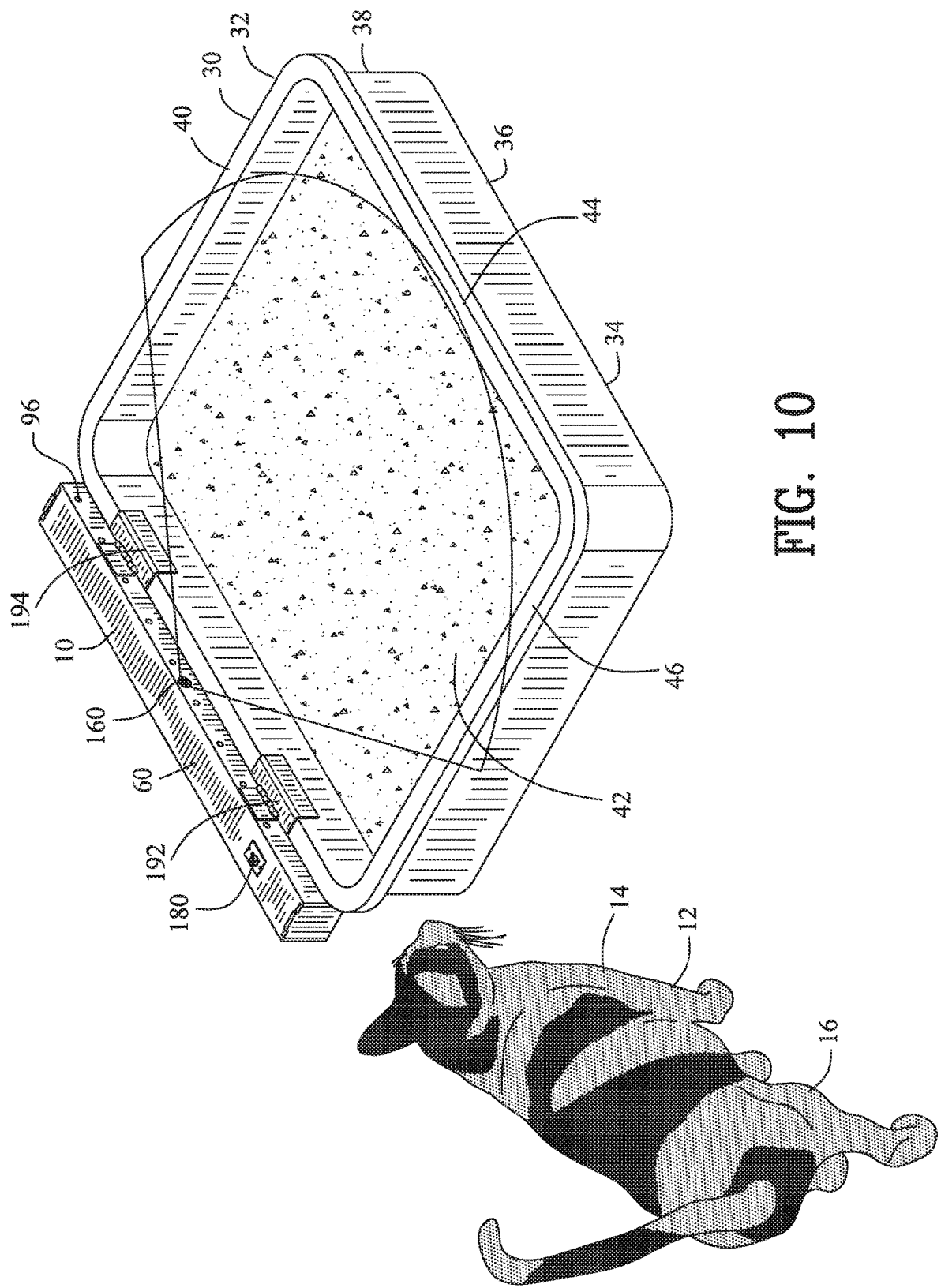
FIG. 10 is a view similar to FIG. 6 illustrating a cat approaching the clean animal container.
Figure 11:
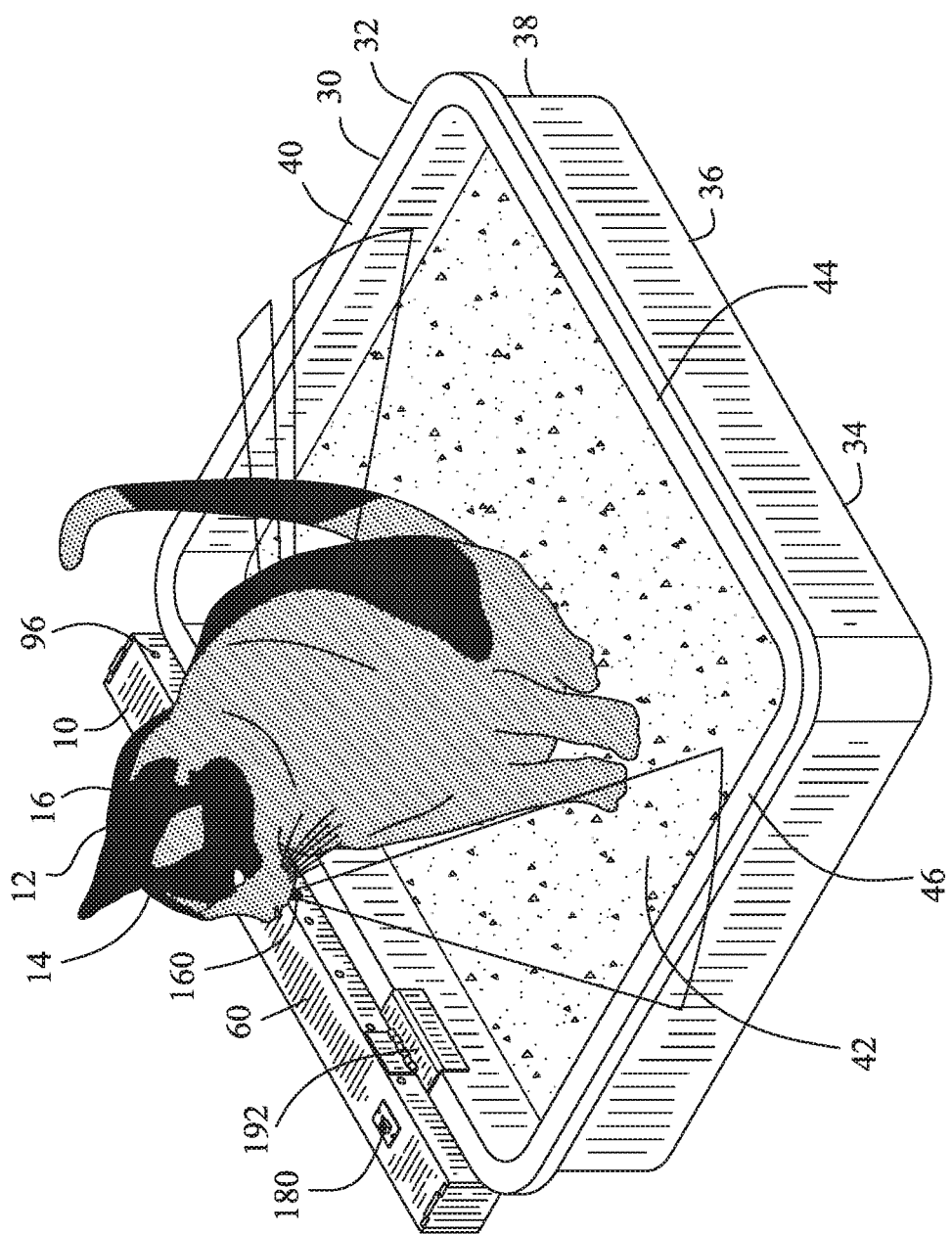
FIG. 11 is a view similar to FIG. 10 illustrating a motion sensor determining the presence of the cat within the animal container.
Figure 12:
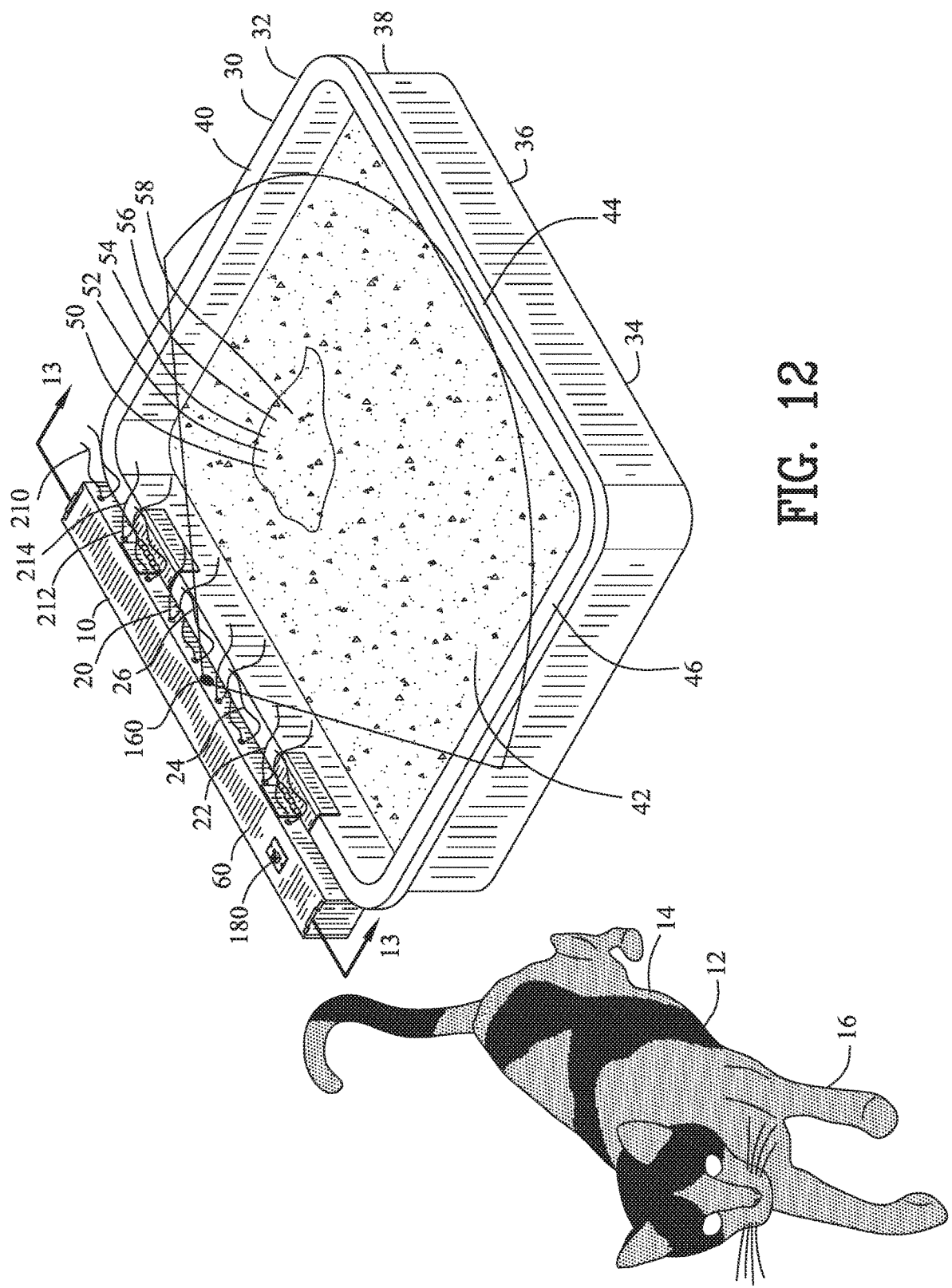
FIG. 12 is a view similar to FIG. 11 illustrating the cat producing a waste product within the animal container, and thereafter the odor treatment dispenser device dispensing an odor treatment substance for treating the odor.

FIGS. 1-14 illustrate an odor treatment dispenser device 10. The odor treatment dispenser device 10 dispenses an odor treatment substance 20. The odor treatment dispenser device 10 is illustrated in FIGS. 6, 9-12 for engaging an animal container 30 and treating an odor 50. However, the odor treatment dispenser device 10 may be utilized for other purposes including but not limited to a room deodorizer, a bathroom deodorizer or a trash container deodorizer.

The animal container 30 as shown in FIGS. 6, 9-12 illustrates a cat litter box 32. The cat litter box 32 has a tray 34 defining a base layer 36 and a perimeter wall 38. The perimeter wall 38 may include an upper lip 40. The cat litter box 32 contains cat litter 42 for treating animal waste 52. The animal waste 52 may include urine 52 and/or feces 54 for an animal 12 including but not limited to a cat 14 or other living organism 16. The urine 52 and feces 54 discharge a cat waste odor 58. The odor treatment dispense device 10 may be utilized for treating the cat waste odor 58 discharged from the urine 52 and/or feces 54 within the animal container 30.

As shown in FIGS. 1-14, the odor treatment dispenser device 10 comprises a housing 60 extending between a primary end 62 and a secondary end 64 and defining a housing chamber 66 within. The primary end 62 has a primary aperture 70. The secondary end 64 has a secondary aperture 72. A canister channel 80 is within the housing chamber 66 and extends between a proximal end 82 and a distal end 84. The proximal end 82 of the canister channel 80 is coupled to the secondary aperture 72. The distal end 84 of the canister channel 80 includes a nozzle aperture 86.

A manifold channel 90 is within the housing chamber 66 and extends between a proximal end 92 and a distal end 94. A plurality of manifold apertures 96 extend from the manifold channel 90 and traverses the housing 60. The nozzle aperture 86 and the manifold channel 90 are coupled by a coupling channel 98.

An electronic channel 100 is within the housing chamber 66 and extends between a proximal end 102 and a distal end 104. The proximal end 102 of the electronic channel 100 is coupled to the primary aperture 70. The distal end 104 of the electronic channel 100 includes an actuator aperture 106.

A canister 110 contains the odor treatment substance 20. The canister 110 is positioned within the canister channel 80. A nozzle 112 is coupled to the canister 110 for dispensing the odor treatment substance 20 from the canister 110. As shown in FIGS. 5 and 13, the nozzle 112 traverses the nozzle aperture 86 and is positioned within the coupling chamber 98. The canister 110 may include a replaceable pressurized aerosol cartridge 114. More specifically, the replaceable pressurized aerosol cartridge 114 may be removably coupled to the canister channel 80 from the secondary aperture 72. The replacement of the canister 110 would be necessary if the canister 110 would become empty. The user may replace the empty canister 110 with a fully filled canister 110 so as to continue used of the odor treatment dispenser device 10.

The odor treatment substance 20 may include a liquid 22, gas 24 or the combination thereof. The liquid 22 may include but not limited to chlorine dioxide 26. Other suitable odor neutralizing substances may be utilized to eliminating the odor 50.

An electronic controller 120 is positioned within the electronic channel 100. The electronic controller 120 may include a circuit board 122 including a plurality of electrical components 124 and/or microchips 126. An actuator 130 is coupled to the electronic controller 120 and traverses the actuator aperture 106. The actuator 130 may include a solenoid switch 132 having a linear displacement arm 134. Alternatively, the actuator 130 may include other electrical actuators that include a displaceable mechanism. The electronic controller 120 activates the actuator 130 for depressing the nozzle 112 and dispenses the odor treatment substance 20 through the plurality of manifold apertures 96 and into the animal container 30 for treating the odor 50. More specifically, upon engagement of the solenoid switch 132, the linear displacement arm 134 is extended from the electronic controller 120. The extending linear displacement arm 134 depresses the nozzle 112 of the canister 110 for opening the valve 116 of the canister 110 and dispenses the odor treatment substance 20. Upon disengagement of the solenoid switch 132, the linear displacement arm 134 is retracted towards the electronic controller 120. The retracting linear displacement arm 134 disengages with the nozzle 112 of the canister 110 for closing the valve 116 of the canister 110 and terminating dispensing of the odor treatment substance 20.

The electronic controller 120 may be supplied with current by direct current or alternating current. For example, the current may include an electrical outlet having 120 volts with or without an electrical transformer. Alternatively, the current may include a replaceable battery 140 positioned through the primary aperture 70 and into the electronic channel 100. The replaceable battery 140 may include a D size dry cell battery 142. The replaceable battery 140 may include other dry cell batteries. The replaceable battery 140 is electrically coupled to the electronic controller 120 for providing an electric current 144 to the electronic controller 120.

A removable primary closure 150 engages the primary end 62 for covering the primary aperture 70 and enclosing the replaceable battery 140. Similarly, a removable secondary closure 152 engages the secondary end 64 for covering the secondary aperture 72 and enclosing the replaceable pressurized aerosol cartridge 114. More specifically, removable primary closure 150 and the removable secondary closure 152 may include a closure wall 154 having a pivot couple 156 and a battery clip keeper 158.

A motion sensor 160 maybe coupled to the housing 60 for determining the presence of the animal 12 within the animal container 30. The motion sensor 160 is electrically coupled to the electronic controller 120 for signaling to the electronic controller 120 of the presence of the animal 12 within the animal container 30. The motion sensor 160 may include passive infrared, optical, microwave, acoustic sensor or ultrasonic.

A timer 170 maybe electrically coupled to the electronic controller 120. The timer 170 has a timer activation point 172. The timer activation point 172 is defined by a time interval after the egress of the animal 12 from the animal container 30. The timer activation point 172 signals to the electronic controller 120 to initiate activation of the actuator 130 for depressing the nozzle 112.

An electrical switch 180 maybe secured to the housing 60. The electrical switch 180 is electrically coupled to the electronic controller 120 for manually activating and deactivating the electronic controller 120.

The odor treatment dispenser device 10 may further include a fastener 190 for coupled to the housing 60 to the animal container 30. More specifically, the fastener 190 may include a first mounting bracket 192 and a second mounting bracket 194. The first mounting bracket 192 and the second mounting bracket 194 include a spring loaded clip 196 coupling an operating arm 198 and a hanger arm 200. As best shown in FIG. 7, the spring loaded clip 196 provides a clockwise rotation force 202 to the first mounting bracket 192 and the second mounting bracket 194. An opposing force 204 as shown in FIG. 8 is applied to the operating arm 198 for overcoming the clockwise rotation force 202 for creating a mounting channel 206 between the hanger arm 200 and the housing 60. As shown in FIG. 9, upon the hanger arm 200 positioned over the upper lip 40 of the animal container 30, the opposing force 204 may be removed. Thereafter, the spring loaded clip 196 applies a compressive force against the upper lip 40 of the animal container 30 for preventing inadvertent removal of the housing 60 from the animal container 30.

As best shown in FIGS. 1, 3-6 and 10-12, the plurality of manifold apertures 96 extend substantially from the primary end 62 to the secondary end 64 of the housing 60 for defining a substantially continuous odor treatment layer 210 being dispensed from the plurality of manifold apertures 96 upon depressing the nozzle 112. The substantially continuous odor treatment layer 210 has a layer width 212, a layer length 241 and a layer depth 216. Preferably the length of the plurality of manifold apertures 96 is commensurate with the length of the animal container 30 such that independent of the location of the animal waste 52 within the animal container 30, the substantially continuous odor treatment layer 210 will contact both the animal waste 52 and the odor 50 for neutralizing the same. More specifically, the layer width 212 and the layer length 241 of the substantially continuous odor treatment layer 210 is preferably commensurate with the container width 44 and the container length 46 of the animal container 30.

Figure 21:
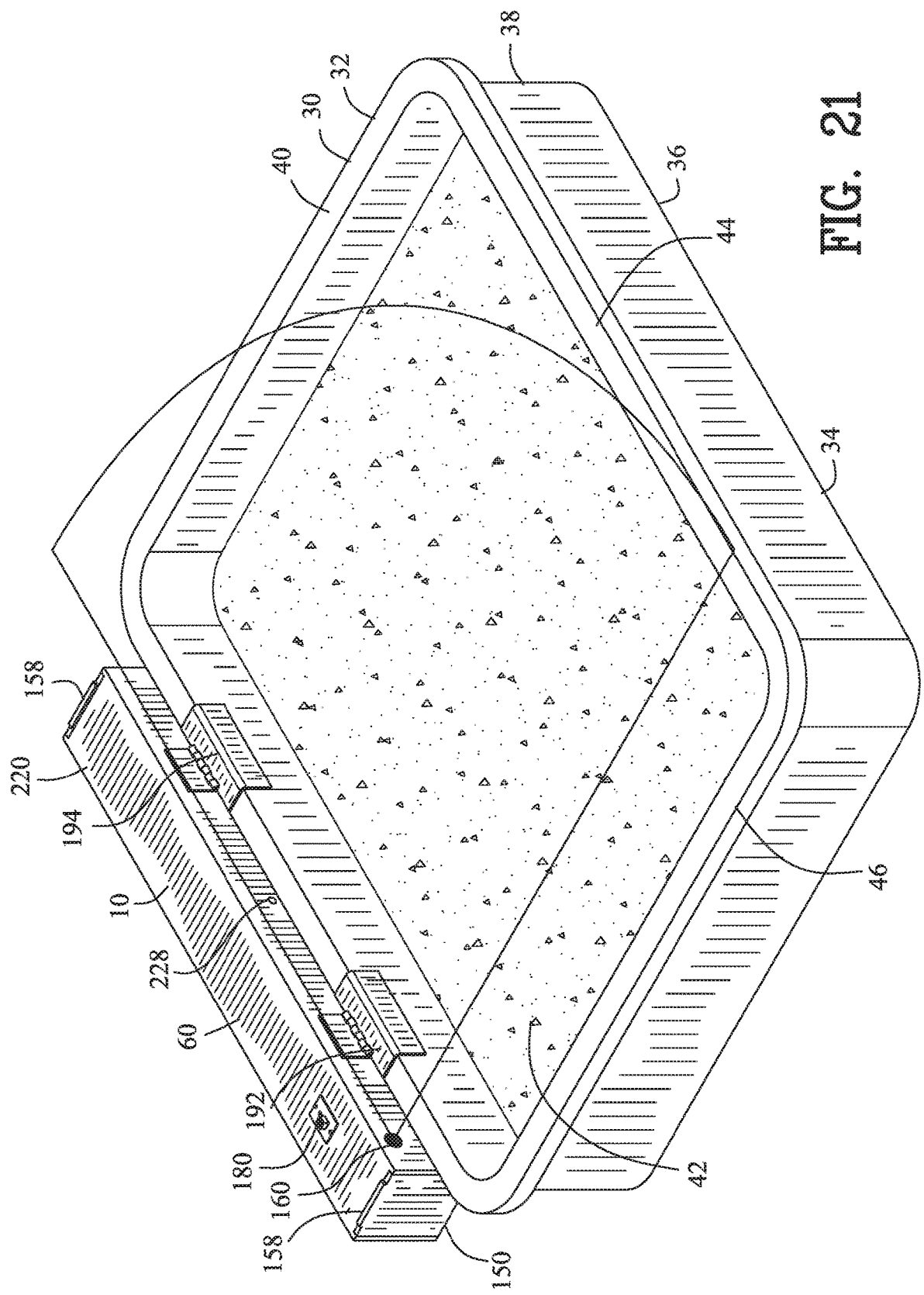
FIG. 21 is a view similar to FIG. 15 with the second embodiment for an odor treatment dispenser device engaging an animal container.

FIGS. 15-24 illustrate a second embodiment 220 of the present invention. A housing aperture 228 traverses the housing 60. The canister 110 is inserted into the secondary aperture 72 for positioning the canister 110 within the housing chamber 66 and aligning the nozzle 112 with the housing aperture 228. The nozzle 112 preferably includes a fan shaped spray pattern have a width of about 16" and a depth between 8" to 12". The housing aperture 228 may include a elliptical shape or a elongated shape to permit the fan shaped spray pattern to exit the housing 60 without contact with the housing 60.

A motor 230 is positioned in the housing chamber 66 for providing a first rotational force 224 and a second rotational force 226. The motor 230 may include a RS-555PH-3255 with 12-24 VDC operating on 3 VDC. A motor controller circuit 222 is electrically coupled to the motor 234 initiating and terminating the first rotational force 224 and the second rotational force 226. A motor shaft 232 extends from the motor 230 and is coupled to a housing actuator 270. The housing actuator 270 slidably engages within the housing chamber. More specifically, the housing actuator 270 may include an actuator base 272 and an actuator shaft 276. A threaded aperture 274 is within the actuator base to 272 of the housing actuator 270. A shaft coupling 260 couples the motor shaft 232 with a threaded pin 262. The threaded pin 262 threadably engages within the threaded aperture 274.

The first rotational force 224 which preferably causes a counterclockwise rotation of the threaded pin 262 creates an expanding displacement 290 of the housing actuator 270 relative to the motor 234 for engaging the housing actuator 270 with the nozzle 112 and thereafter dispensing the odor treatment substance 20 from the canister 110 and to the exterior of the housing 60. The second rotational force 226 which preferably causes a clockwise rotation of the threaded pin 262 creates a retracting displacement 292 of the housing actuator 270 relative to the motor 234 for disengaging the housing actuator 270 with the nozzle 112 and terminating the dispensing of the odor treatment substance 20 from the canister 110.

The replaceable battery 140 is electrically coupled to the motor controller circuit 222 for powering the motor 230. The replaceable battery 140 may include a CR 123a Lithium 3 VDC. Similarly, the motion sensor 160 is electrically to the motor controller circuit 222 for activating and deactivating the motor 230. Preferably, the motion sensor 160 provides a 90° motion sensing field. The motion sensor 160 may include passive infer red (PIR) sensor ST-00082 utilizing a AM322 sensor chip. A timer 170 is electrically coupled to the motor controller circuit 222. The timer 170 has a timer activation point 172. The timer activation point 172 is defined by a time interval after the motion sensor 160 senses an object. After the time interval as passed the motor controller circuit 222 activates the motor 230. The electrical switch 180 is electrically coupled motor controller circuit 222 for manually activating and deactivating the motor 230.

The second embodiment may further include an internal mounting bracket 240 coupled to the housing 60 within the housing chamber 66. The internal mounting bracket 240 including a motor leg 242, a base leg 244, a first leg wall 246 and a second leg wall 248. The motor leg 242, the base leg 244, the first leg wall 246 and the second leg wall 248 may be constructed of a integral one piece metallic plate that is bent into the final configuration. The motor leg 242 and the base leg 244 may be reinforced by side plates wherein a first bracket fastener 256 and a second bracket fastener 258 traverses the side plates for reinforcing the motor leg 242 relative to the base leg 244. The motor 230 is coupled to the motor leg 242 for mounting the motor 230 within the housing chamber 66.

The first leg wall 246 and the second leg wall 248 define a leg channel 250 therebetwen. The actuator shaft 276 extends into the leg channel 250. An actuator wheel 282 encircles the actuator shaft 276. The actuator wheel 282 is positioned within the leg channel 250 and adjacent to the first leg wall 246 and the second leg wall 248 for preventing an angular displacement of the housing actuator 270 relative to the housing 60.

A first stopping pin 252 is coupled between the first leg wall 246 and the second leg wall 248. The actuator shaft 276 engages the first stopping pin 252 in a terminal retracting position 294 of the housing actuator 270. A second stopping pin 254 is coupled between the first leg wall 246 and the second leg wall 248. The actuator shaft 276 engages the second stopping pin 254 in a terminal expanding position 296 of the housing actuator 270. An actuator bumper 280 may further encircle the actuator shaft 276 for cushioning the contact between the actuator shaft 276 with the first stopping pin 252 in the terminal retracting position 294 and the actuator shaft 276 with the second stopping pin 254 in the terminal expanding position 296. The actuator bumper 280 may include a portion tuber tubing.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An odor treatment dispenser device for an animal container, the odor treatment dispenser device comprising:
    a housing extending between a primary end and a secondary end and defining a housing chamber;
    said primary end having a primary aperture;
    said secondary end having a secondary aperture;
    a canister channel within said housing chamber and extending between a proximal end and a distal end;
    said proximal end of said canister channel coupled to said secondary aperture;
    said distal end of said canister channel including a nozzle aperture;
    a manifold channel within said housing chamber and extending between a proximal end and a distal end;
    a plurality of manifold apertures extending from said manifold channel and traversing said housing;
    an electronic channel within said housing chamber and extending between a proximal end and a distal end;
    said proximal end of said electronic channel coupled to said primary aperture;
    said distal end of said electronic channel including an actuator aperture;
    a canister containing an odor treatment substance positioned within said canister channel; a nozzle coupling to said canister and traversing said nozzle aperture;
    said nozzle dispensing said odor treatment substance from the canister;
    an electronic controller positioned within said electronic channel;
    an actuator coupling to said electronic controller and traversing said actuator aperture; and
    said electronic controller activating said actuator for depressing said nozzle and dispensing said odor treatment substance through said plurality of manifold apertures and into the animal container for treating the odor.

2. An odor treatment dispenser device as set forth in claim 1, further including a replaceable battery positioned through said primary aperture and into said electronic channel; and
    said replaceable battery electrically coupled to said electronic controller for providing a electric current to said electronic controller.

3. An odor treatment dispenser device as set forth in claim 2, further including a removable primary closure engaging said primary end for covering said primary aperture and enclosing said replaceable battery.

4. An odor treatment dispenser device as set forth in claim 1, wherein said canister includes
    a replaceable pressurized aerosol cartridge; and
    said replaceable pressurized aerosol cartridge removably coupled to said canister channel.

5. An odor treatment dispenser device as set forth in claim 4, further including a removable secondary closure engaging said secondary end for covering said secondary aperture and enclosing said replaceable pressurized aerosol cartridge.

6. An odor treatment dispenser device as set forth in claim 1, wherein said odor treatment substance includes a liquid; and
    said liquid includes chlorine dioxide.

7. An odor treatment dispenser device as set forth in claim 1, wherein said plurality of manifold apertures extend substantially from said primary end to said secondary end of said housing defining a substantially continuous odor treatment layer being dispensed from said plurality of manifold apertures upon depressing said nozzle.

8. An odor treatment dispenser device as set forth in claim 1, further
    including a motion sensor coupled to said housing for determining the presence of an animal within the animal container; and
    said motion sensor electrically coupled to said electronic controller for signaling to said electronic controller of the presence of the animal within the animal container.

9. An odor treatment dispenser device set forth in claim 8, further including
    a timer electrically coupled to said electronic controller;
    said timer having a timer activation point;
    said timer activation point defined by a time interval after the egress of the animal from the animal container; and
    said timer activation point signaling to said electronic controller to initiate activation of said actuator for depressing said nozzle.

10. An odor treatment dispenser device as set forth in claim 1, further including an electrical switch coupled to said housing; and
    said electrical switch electrically coupled to said electronic controller for manually activating and deactivating said electronic controller.

11. An odor treatment dispenser device as set forth in claim 1, further including a fastener coupled to said housing; and
    said fastener engaging the animal container for supporting said housing.

12. An odor treatment dispenser device for an odor, comprising:
    a housing extending between a primary end and a secondary end and defining a housing chamber;
    said primary end having a primary aperture;
    said secondary end having a secondary aperture;
    a canister channel within said housing chamber and extending between a proximal end and a distal end;
    said proximal end of said canister channel coupled to said secondary aperture;
    said distal end of said canister channel including a nozzle aperture;
    a manifold channel within said housing chamber and extending between a proximal end and a distal end;
    a plurality of manifold apertures extending from said manifold channel and traversing said housing;

an electronic channel within said housing chamber and extending between a proximal end and a distal end;

said proximal end of said electronic channel coupled to said primary aperture;

said distal end of said electronic channel including an actuator aperture;

a canister containing an odor treatment substance positioned within said canister channel; a nozzle coupled to said canister and traversing said nozzle aperture;

said nozzle dispensing said odor treatment substance from said canister;

an electronic controller positioned within said electronic channel;

an actuator coupled to said electronic controller and traversing said actuator aperture; and said electronic controller activating said actuator for depressing said nozzle and dispensing said odor treatment substance through said plurality of manifold apertures for treating the odor.

\* \* \* \* \*